(12) United States Patent
Torres et al.

(10) Patent No.: US 10,383,667 B2
(45) Date of Patent: Aug. 20, 2019

(54) BONE PLATE SYSTEM WITH INSERTS FOR CONTACTING AN ADJACENT BONE SURFACE

(71) Applicant: Stryker European Holdings I, LLC, Kalamazoo, MI (US)

(72) Inventors: Milton Torres, Muri B. Bern (CH); Axel Bernhard Cremer, Pleasantville, NY (US); Kennan Hanson, Sloatsburg, NY (US); Yuri Zaitsev, Nyack, NY (US); Zongtau Zhang, Riverdale, NJ (US); Jan Heinsohn, Hoboken, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 183 days.

(21) Appl. No.: 15/229,966

(22) Filed: Aug. 5, 2016

(65) Prior Publication Data

US 2018/0036047 A1 Feb. 8, 2018

(51) Int. Cl.
*A61B 17/80* (2006.01)

(52) U.S. Cl.
CPC ............ *A61B 17/809* (2013.01); *A61B 17/80* (2013.01); *A61B 17/8033* (2013.01)

(58) Field of Classification Search
CPC ............................... A61B 17/80; A61B 17/809
See application file for complete search history.

(56) References Cited

U.S. PATENT DOCUMENTS

| | | | |
|---|---|---|---|
| 5,098,434 A * | 3/1992 | Serbousek | A61B 17/8625 606/308 |
| 5,190,545 A | 3/1993 | Corsi et al. | |
| 5,474,553 A * | 12/1995 | Baumgart | A61B 17/80 606/309 |
| 5,578,034 A * | 11/1996 | Estes | A61B 17/8047 411/909 |
| 6,017,345 A * | 1/2000 | Richelsoph | A61B 17/7059 606/246 |
| 8,142,485 B2 | 3/2012 | Buhren et al. | |
| 8,343,155 B2 * | 1/2013 | Fisher | A61B 17/80 606/74 |
| 2004/0254579 A1 | 12/2004 | Buhren et al. | |
| 2010/0082070 A1 | 4/2010 | Diez | |
| 2012/0184960 A1 | 7/2012 | Dosta | |
| 2017/0333098 A1* | 11/2017 | Vasta | A61B 17/8047 |

FOREIGN PATENT DOCUMENTS

EP 0897697 A1 2/1999

OTHER PUBLICATIONS

Extended European Search Report for Application No. EP17000641.5 dated Oct. 25, 2017.

* cited by examiner

*Primary Examiner* — Christopher J Beccia
(74) *Attorney, Agent, or Firm* — Lerner, David, Littenberg, Krumholz & Mentlik, LLP

(57) ABSTRACT

The disclosure relates to a bone plate systems and method. A system comprises a bone plate having a bone facing side, a front side being arranged substantially opposite to and facing away from the bone facing side, and at least one insert receiving portion, the system further comprising at least one insert defining a contacting region for contacting an adjacent bone surface and being releasably receivable in said insert receiving portion, wherein the insert is insertable into the insert receiving portion from the bone facing side.

21 Claims, 4 Drawing Sheets

BONE PLATE SYSTEM WITH INSERTS FOR CONTACTING AN ADJACENT BONE SURFACE

TECHNICAL FIELD

The present disclosure generally relates to bone plate systems. In particular, bone plate systems and methods for operating same are described.

BACKGROUND OF THE INVENTION

To promote the healing process of a damaged or fragmented bone, bone plates are commonly attached to an outside surface of the bone. The bone plates act as stabilizing elements for the damaged area. In addition, they may help to position fragmented bone sections relative to one another.

Depending on the specific bone fragmentation, suitable bone plates are generally selected based on the shape, size or other relevant characteristics. Accordingly, bone plates are mostly designed for a limited range of uses or only for specific types of injuries. Therefore, the field of application of such bone plates is often limited.

BRIEF SUMMARY OF THE INVENTION

According to one aspect, a bone plate system is provided, comprising: a bone plate having a bone facing side, a front side being arranged substantially opposite to and facing away from the bone facing side, and at least one insert receiving portion, the bone plate system further comprising at least one insert defining a contact or contacting region for contacting an adjacent bone surface and being releasably receivable in said insert receiving portion, wherein the insert is insertable into the insert receiving portion from the bone facing side.

The bone plate may be elongated and/or generally configured with a rectangular or oval outline, said outline confining or being defined by at least one of the front side or the bone facing side. Furthermore, the bone plate can be anatomically pre-shaped (e.g. bent or curved). Still further, the bone plate may comprise or be produced from metallic and/or plastic materials.

In a state in which the bone plate is arranged at a bone to be treated, the front side may face away from the bone and, for example, face a surgeon arranging said bone plate at the bone. The bone facing side, on the other hand, may lie opposite to and/or at least partially abut against an adjacent surface of the bone.

As further detailed below, the insert receiving portion may generally comprise or be formed by a free space within the bone plate. Accordingly, it may comprise recesses, holes or the like in which the insert is arrangeable.

In general, a plurality of insert receiving portions may be provided, for example between 2 and 20, 5 and 20, 2 and 10 or 3 and 8. In one example, at least some of the insert receiving portions are distributed along a common axis of the bone plate, such as its longitudinal axis. Likewise, a plurality of inserts may be provided for being inserted into each or only selected ones out of said plurality of insert receiving portions. Also, in case of a plurality of inserts, these may generally be equivalent or differ from one another, in particular with regard to the size, shape or design of their bone contacting regions.

The inserts may equally comprise metallic and/or plastic materials. Apart from the contacting region for contacting the adjacent bone surface, they may also comprise a coupling portion for interacting with the insert receiving portion. The contacting region can comprise or be formed by a portion of the insert which is arranged to face (and contact) an adjacent bone surface when the insert is inserted in the insert receiving portion. Accordingly, the contacting region may define an area of contact between the insert and the bone to be treated.

Furthermore, the contacting region may comprise a substantially planar and/or flat contacting surface, the size of said contacting surface preferably corresponding to an area of contact between the insert and bone. Likewise, the contacting region may be configured with a varying height profile (i.e., being non-planar). For example, the contacting region may comprise indentations, protrusions, elevations or similar structures affecting its height-profile. In this case, only some parts of the contacting regions can actually be configured to contact the bone (at least during an initial healing stage in which no bone ingrowth takes place). Accordingly, the area of contact between the contacting region and bone may be formed by an area comprising the single points of contact between the non-planar contacting surface and the bone.

In one example, the contacting region of the insert may define an area of contact which has a size of between 5% and 75% of an area of the bone facing side, said latter area being e.g. defined by an area of an external surface of said bone facing side. Alternatively, the area of contact may have a size of between 5% and 50%, 5% and 25% or 10% and 20% of the area of the bone facing side.

In the context of receiving the insert in the insert receiving portion, the term "releasably received" may include the insert being releasable from said insert receiving portion in a substantially non-destructive manner. The non-destruction may in particular relate to the insert as such (or at least to its contacting region) and/or to the insert receiving portion or bone plate. Preferably, this also includes a non-destruction of any coupling of fixing structures between the insert and insert receiving portion (e.g., no glue or material layers which need to be broken up). In one example, the insert is insertable and releasable from the insert receiving portion by way of sliding motions or by way of respective push/pull-motions, said motions preferably taking place along a common insertion axis.

Still further, due to being insertable into the insert receiving portion from the bone facing side, a surgeon may hold the bone plate with the front side facing him, to then insert the insert substantially from below (i.e., arranging the insert at the bone facing side and then directly sliding it into the insert receiving portion, preferably along a substantially linear insertion axis).

According to a further embodiment, the insert comprises a release portion that is accessible from the front side of the bone plate. This relates in particular to a state in which the insert is inserted into the insert receiving portion and, preferably, the bone plate being arranged at a bone to be treated. In such a state, the release portion may be accessible, for example, for being manually operated by a surgeon. In other words, the release portion may not be covered, blocked or otherwise obstructed but directly accessible from the front side of the bone plate. Accordingly, the release portion may form part of an external portion of the bone plate system close to or at the front side of the bone plate.

Generally, the release portion may comprise any structure which allows for a manipulation, so that the insert is released from the insert receiving portion. For example, the release portion may be configured to receive a pushing, rotating or other suitable force for enabling said release. Also, the release portion may be operable so as to release an engagement between the insert and bone plate (e.g. by releasing a snap-fit connection or other locking engagement between said elements). Again, operating the release portion may be fully performed from the front side of the bone plate. As detailed below, this may also allow for lifting the bone plate from the bone to be treated while simultaneously releasing the inserts therefrom, so that said inserts can remain at the bone.

The bone plate system may further comprise a fixing member receiving portion that is configured to receive a fixing member for securing the bone plate at a bone, the fixing member receiving portion and the insert receiving portion being at least partially separated from one another. As fixing members, screws may be applied which can be inserted into through-holes of the bone plate system and then screwed into an adjacent bone portion. Likewise, circumferential wires can be wound around a cross-section of the bone and the bone plate when arranged at the bone. The wires can then be tightened to secure the bone plate at the bone and to avoid a relative movement therebetween.

It is known to provide suitable receiving portions for such fixing members at a bone plate (such as screw-receiving through-holes or guiding channels/tracks for the circumferential wires). Yet, according to the present aspect, the inserts can be configured to be generally spaced apart from such fixing members and/or fixing member receiving portions. Likewise, the inserts may generally be configured to not directly contact such fixing members and/or being free of directly interacting with such fixing members (e.g. not directly guiding/receiving them and/or not directly exchanging forces therewith). Also, the insert may be at least partially releasable from the bone plate independently of the presence of any fixing members. In other words, it may be contemplated to provide a certain degree of functional separation between the insert having a predominantly bone contacting function (i.e., none or only a limited fixing effect) and the fixing members having a predominantly fixing function (i.e., having no or only a limited contact with an external surface of the bone, said surface being covered by the bone plate).

Alternatively, the insert may comprise a fixing member receiving portion that is configured to receive a fixing member for securing the bone plate at a bone. As previously stated, said fixing member receiving portion may comprise a through-hole for a bone screw, preferably including a counterbore or countersunk portion for receiving the bone screw head. Likewise, the fixing member receiving portion may comprise guiding and/or holding portions for circumferential wires, for example channels, tracks, grooves or holding clips. Preferably, the insert comprises a through-hole which when being arranged in the insert receiving portion allows for inserting a bone screw from the front side of the bone plate and moving it towards the bone to be treated. For doing so, said through-hole may extend transversal to and preferably orthogonal to at least one of an external surface area of the bone plate's front side, the bone facing side and the contacting region of the insert.

Note that as a general aspect, the insert receiving portion of the bone plate may be configured to selectively receive either the insert or a bone fixing member, such as a bone screw. This may relate in particular to directly receiving such members, i.e. directly contacting and/or surrounding at least a portion of the insert or bone fixing member, preferably without further members being arranged therebetween. For example, the insert receiving portion may be configured to selectively either directly receive an insert, a bone fixing member or an insert comprising a fixing member receiving portion. For doing so, the bone plate may comprise at least one recess which preferably comprises a through-hole that connects the front side and bone facing side. In general, a bone fixing member (preferably a bone screw) may be directly insertable into the insert receiving portion from the front side and, alternatively, the insert may be inserted into the same insert receiving portion from the bone facing side. For receiving the fixing member, the insert receiving portion of the bone plate may further comprise a diameter-widened portion or diameter step close to or at the front side of the bone plate for receiving a bone screw head. Additionally or alternatively, the insert receiving portion may comprise a countersunk or counterbore-portion for receiving said bone screw head.

In a further embodiment, the insert receiving portion comprises a recess that is connected to the front side. Accordingly, said recess may from a connecting channel between the front side and bone facing side. Preferably, the insert is at least partially arrangeable in said recess close to the front side when being inserted into the bone plate. This way, a release portion of the insert and/or a fixing member receiving portion can be arranged close to or at the front side of the bone plate, for example, by being arranged in said recess and moved to the front side therethrough. Similarly, this may allow for selectively receiving a bone screw or insert in the insert receiving portion as discussed above.

The insert may further be configured to engage with the insert receiving portion. This may include an engagement by means of a press or friction fit and/or a form fit. In one example, one of the insert and insert receiving portion is at least partially elastically deformable and the other of the insert and insert receiving portion is configured to, at least during the insertion, deform the respective elastically deformable member. For doing so, the shapes and/or dimensions of interacting portions of the respective members may be appropriately selected. Additionally or alternatively, an engagement between the insert and insert receiving portion may be formed by means of an undercut, thread or other suitable structures.

In this context, the insert may comprise a stop portion that is configured to abut against the insert receiving portion so as to limit an insertion depth of the insert. For doing so, the stop portion and/or a corresponding abutment surface of the insert receiving portion may be arranged at an angle and preferably substantially orthogonal to an insertion axis along which the insert is moved into the insert receiving portion. The stop portion and abutment surface of the insert receiving portion may form a substantially planar contacting region. In one example, the abutment surface of the insert receiving portion forms part of or is connected to the bone facing side of the bone plate.

At least one of the insert and insert receiving portion may further comprise a locking portion for being lockable with the respective other of the insert and insert receiving portion. The locking portion may be configured as a flexible and/or elastically deformable portion, e.g. for engaging with an undercut of the respective other of the insert and insert receiving portion. Accordingly, the locking portion may comprise a snap-fit portion which, e.g. after an initial deformation and/or deflection during insertion of the insert into the insert receiving portion, may come into a locking engagement with a corresponding receiving portion of the other member. Said engagement may again comprise a press and/or form fit. Alternatively, the locking portion may be configured as a substantially rigid portion to engage with a rigid or flexible and/or elastically deformable receiving portion of the respective other of the insert and insert receiving portion.

According to a further aspect, the contacting region of the insert is configured to extend beyond at least an adjacent portion of the bone facing side towards an adjacent bone surface. To put it differently, the contacting region may form a local protrusion at the bone facing side or a locally outermost portion of the bone plate system at the bone facing side. Accordingly, the contacting region may be spaced apart from an external surface of the bone facing side and more closely arranged to a bone to be treated then said external surface. Thus, a gap may be formed between an area of contact of the insert's contacting region and at least an adjacent or surrounding portion of the bone facing side, such that the contacting region protrudes towards an adjacent bone surface.

Note that it is equally contemplated that the contacting region extends beyond the whole of the bone facing side towards an adjacent bone surface, i.e., not only forms a local protrusion or local outermost portion at said bone facing side but generally spaces the bone facing side apart from an adjacent bone surface. The contacting region may hence generally be configured to lift the bone facing side off a bone surface to be treated and arrange it at a distance thereto (i.e., act as a spacer member between bone plate and bone).

Alternatively, the contacting region can be configured to be flush with at least an adjacent portion the bone facing side. This may include that an external surface of the bone facing side and the contacting region substantially extend in one common plane. Again, this may also relate to the bone facing side as a whole, so that the contacting region according to this aspect may not form any substantial protrusion at said bone facing side but is rather substantially level therewith.

According to a further embodiment, the contacting region is larger than the insert receiving portion. Accordingly, the contacting region and/or its area of contact to the bone may exceed in area defined by the insert receiving portion. Specifically, the contacting region and/or the area of contact may exceed a largest cross-section of said insert receiving portion. Said cross-section may extend substantially in parallel to the contacting region and/or extend at an angle to the insertion axis along which the insert is moved when being arranged in the insert receiving portion. Similarly, the contacting region may exceed a cross-section of a coupling portion of the insert which is directly inserted and received in the insert receiving portion. Accordingly, the insert may generally be configured with a T-shaped cross-section. Also, it may be inserted into the insert receiving portion such that when being arranged at a bone, said T-shape is substantially inverted.

In a further example, the contacting region comprises a plurality of protruding members that are arranged to protrude towards an adjacent bone surface. As explained above, said protruding members may form single points of contact between the insert and the bone and an area of contact defined by the contacting region preferably comprises each of said points of contact. Accordingly, the protruding members may generally act as spacer members between the insert and adjacent bone surface. Also, they may be configured to reduce the direct surface contact between the insert and the bone surface. Preferably, the protruding members comprise spikes which may be marked by a decreasing cross-section towards their free ends, so as to be generally pointed or sharp.

The contacting region may further comprise a bone ingrowth portion. In this case, the insert may generally be configured to, at least after some time of contacting a bone to be treated, connect with the recovering bone tissue. The bone ingrowth portion may form at least part of an area of contact between the contacting region and e.g. form a bone ingrowth surface at the contacting region. Alternatively or additionally, the bone ingrowth portion may be provided at a free end of at least one protruding member of the contacting region as discussed above. For promoting the ingrowth of bone tissue, said portion may generally comprise free spaces, such as recesses or holes, into which the tissue can grow. Likewise, said portion may have an irregular or rough surface texture or generally comprise protruding and/or undercutting portions which can be surrounded by ingrowing bone tissue. Accordingly, said bone ingrowth portion may generally form an outermost or external surface portion of said contacting region. The bone ingrowth portion may further comprise a biodegradable material, so as to after some time and preferably after an ingrowth of bone tissue has already taken place start to degrade.

In one example, the contacting region comprises a porose material. Similar to above, said porose material may serve as or be comprised by a bone ingrowth portion and thus be configured to directly contact and engage with the recovering bone tissue. For doing so, it is preferably arranged in an outermost or external surface portion of the contacting region.

The disclosure further relates to a method of operating a bone plate system, said bone plate system comprising a bone plate having a bone facing side, a front side being arranged substantially opposite to and facing away from the bone facing side, and at least one insert receiving portion, the bone plate system further comprising at least one insert defining a contacting region for contacting an adjacent bone surface and being releasably receivable in said insert receiving portion, the method comprising the steps of:

arranging the bone plate such that the contacting region abuts against an adjacent bone surface;

securing the bone plate at the bone by way of at least one fixing member;

removing the fixing member and releasing the insert from the bone plate, so that the bone plate can be removed from the bone while the insert remains thereat.

In this context, the bone plate system may be configured according to any of the further aspects discussed above. The same applies to the fixing members which may again be configured as bone screws, circumferential wires or the like. Also, said fixing members may either be inserted into separate fixing member receiving portions of the bone plate or into respective receiving portions in the inserts. Moreover, the inserts may be provided with bone ingrowth portions as discussed above so that (at least after some time has passed after arranging the bone plate at the bone) the inserts may be held at the bone by means of partially ingrown bone tissue. Also, the insert as a whole or at least the bone ingrowth portions thereof may be biodegradable.

The method may further comprise a step of inserting the inserts into the insert receiving portion from the bone facing side prior to arranging the bone plate at the bone. Furthermore, for releasing the insert from the bone plate, a release portion thereof may be operated from the bone plate's front side. Also, the steps are preferably carried out in the order as listed above, whereas between the steps of securing the bone plate at the bone and again removing it therefrom, a certain amount of time may pass, such as several days, weeks or months.

Note that the method may generally comprise any further steps to achieve any of the effects or provide any of the operating states of the bone plate system as indicated above and as further discussed below with respect to the figures.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1A:
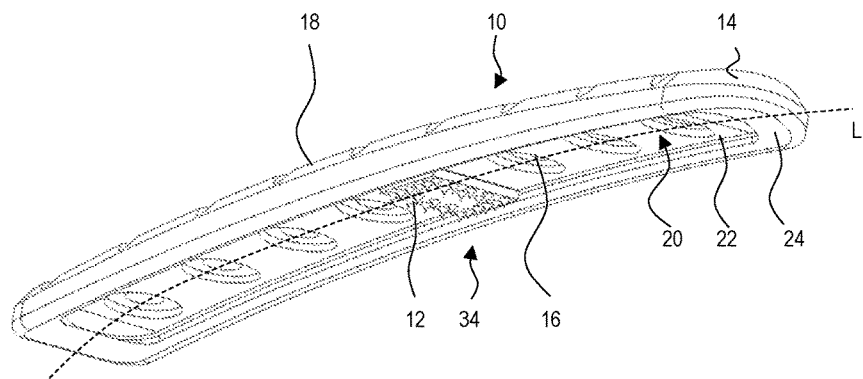
FIGS. 1a-1d show views of a bone plate system according to a first embodiment.

In the following, embodiments of a bone plate system will be described. The same reference numerals will be used to denote the same or similar structural features.

Figure 1B:
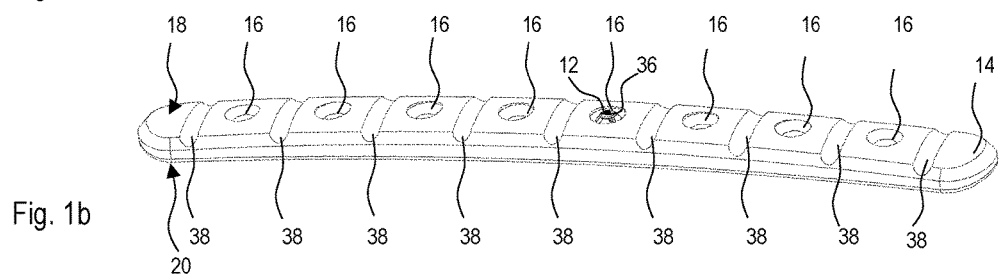
Figure 1C:
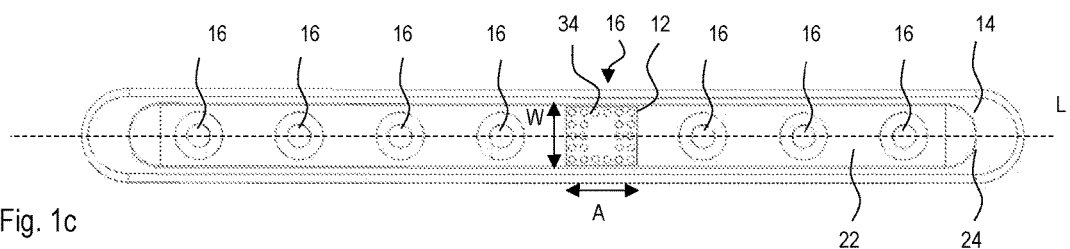
Figure 1D:
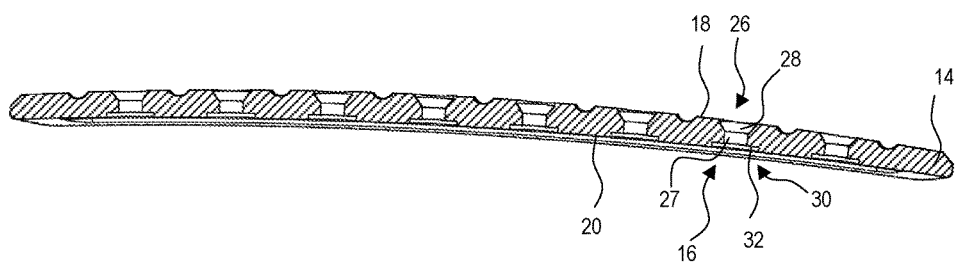

FIGS. 1a-1d show views of a bone plate system 10 according to a first embodiment. More specifically, FIGS. 1a-1c show different perspective views of the bone plate system 10, comprising an insert 12 which is attached to a bone plate 14 by arranging it in a bone plate receiving portion 16. FIG. 1d, on the other hand, shows a cross-sectional view along a longitudinal axis L of the bone plate 14 in a state with no insert 12 being inserted therein.

As can be gathered from FIG. 1a, the bone plate 14 is generally configured as an elongated member extending along a longitudinal axis L. Also, the bone plate 14 has a rectangular shape with rounded axial end sections (see also FIG. 1c). The bone plate 14 further has a front side 18 which faces away from the viewer in FIG. 1a and can better be seen in FIG. 1b. Opposite to said front side 18, the bone plate 14 comprises a bone facing side 20 which is configured to being arranged oppositely to and facing a bone surface to be treated. The bone facing side 20 comprises an elongated recess 22 which extends along the longitudinal axis L and is surrounded by a rim portion 24 (see also FIG. 1c). In said recess 22, a total of eight insert receiving portions 16 is provided with one of which currently receiving an insert 12.

As can best be seen in FIG. 1d, the insert receiving portions 16 each comprise a through-hole 26 extending substantially perpendicular to the longitudinal axis L of the bone plate 14 and connecting the front side 18 and bone facing side 20. At the front side 18, the through-holes 26 comprise a conically-shaped countersunk portion 28 which is shaped to receive a head portion of a non-depicted bone screw. Accordingly, depending on the type of injury to be treated, the insert receiving portions 16 can also be used for directly receiving bones screws and fixing the bone plate 14 in a generally known manner at the bone.

At the bone facing side 20, each insert receiving portion 16 further comprises a circular recess 30 having a larger diameter than e.g. the countersunk portion 28 and a limited depth. As further detailed below, the circular recess 30 thus forms a diameter step in the insert receiving portion 16 which is used as a stop surface 32 for limiting an insertion depth of the inserts 12. Still further, the insert receiving portions 16 each comprise a cylindrical portion 27 connecting the countersunk portion 28 and the circular recess 30, said cylindrical portion 27 defining a smallest diameter and cross-section of the insert receiving portion 16.

Coming back to FIGS. 1a-c, one can see that the insert 12 comprises a contacting region 34 which is arranged so as to face an adjacent bone surface. In other words, the contacting region 34 and the bone facing side 22 (or at least a base region of the recess 22 and/or the rim 24 of the bone facing side 20) are substantially parallel to one another. As further evident from FIG. 1c, the contacting region 34 extends over the complete width W of the recess 22, said width extending orthogonally to the longitudinal axis L. Furthermore, a length A of the contacting region 34 which extends along the longitudinal axis L is chosen so that an area of contact to an adjacent bone surface defined by the contacting region 34 amounts to approximately 10% of the total area of the bone facing side 20.

From FIG. 1b, it can further be gathered that a release portion 36 of the insert 12 (which will be discussed in more detail below) is accessible from the front side 18. More specifically, in the inserted state of the insert 12, said release portion 36 extends through the through-hole 26 of the insert receiving portion 16 and into the countersunk portion 28, so that it can be manually operated from the front side 18.

Still further, the front side 18 comprises several channels 38 which in a known manner define tracks for guiding and receiving non-depicted circumferential wires for securing the bone plate 14 to a bone. As can be seen in FIG. 1b, said channels 38 are spaced apart from the insert receiving portion 16, so that the inserts 12 according to this embodiment do not interact with, contact or receive such wires and are thus generally insertable and releasable from the insert receiving portion 16 independently of the presence of such wires.

Figure 2:
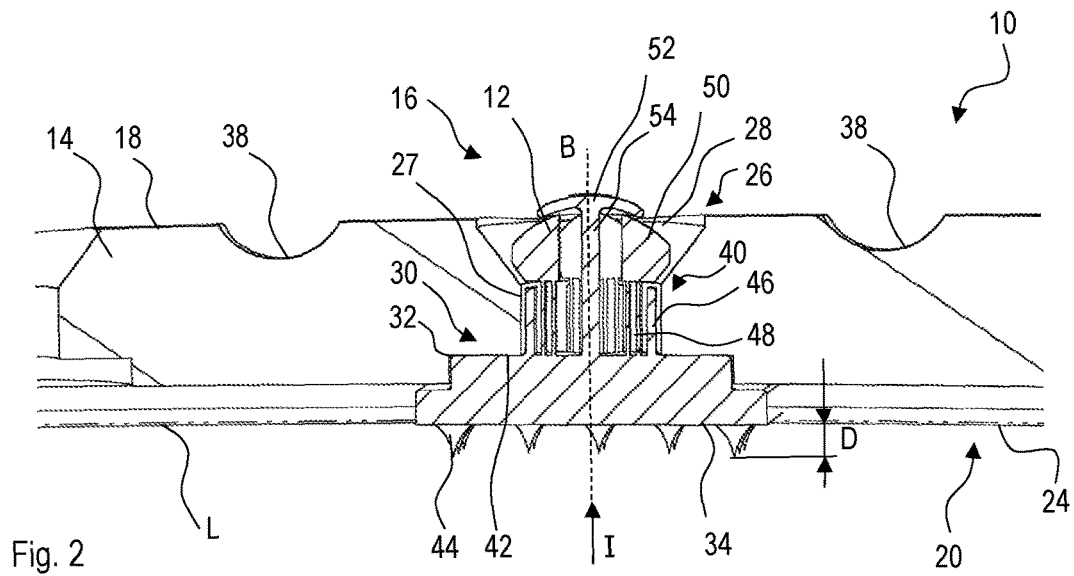
FIG. 2 shows a cross-sectional partial view of the bone plate system according to the first embodiment.

FIG. 2 shows a cross-sectional partial view of the bone plate system 10 according to the first embodiment. More precisely, FIG. 2 shows a cross-sectional view along the longitudinal axis L of the bone plate 14 in the region of the insert 12. Again, one can see the channels 38 for receiving the non-depicted circumferential wires. Furthermore, one can see the insert receiving portion 16 comprising the through-hole 26 as well as the countersunk portion 28, the cylindrical section 27 and the circular recess 30.

The insert 12 comprises the previously discussed release portion 36 which in the inserted state extends into the countersunk portion 28 and slightly beyond an external surface of the front side 18. Furthermore, the insert 12 comprises a coupling portion 40 which is in particular received in the cylindrical section 27 of the insert receiving portion 16. The coupling portion 40 further merges into the contacting region 34 of the insert 12. Note that the coupling portion 40 further comprises a diameter-enlarged stop portion 42 which abuts against the stop surface 32 formed by the circular recess 30 to limit an insertion depth of the insert 12 into the insert receiving portion 16.

From FIG. 2, it can thus be seen that the contacting region 34 generally forms the largest portion of the insert 12, whereas the coupling portion 40 has significantly smaller dimensions (in particular when viewed along the longitudinal axis L or, more precisely, with regard to the diameter of the coupling portion 40 compared to the length A and width W of FIG. 1c). This results in an overall T-shaped cross-section of the insert 12 or, with the orientation as depicted in FIG. 2, an inverted T-shaped cross-section.

This generally allows for inserting the insert 12 into the insert receiving portion 16 from the bone facing side 20 as marked by an arrow I in FIG. 2. Note that different configurations for enabling said insertability from below (i.e., from the bone facing side 20) are equally conceivable.

In other words, the insert 12 can be pushed into the insert receiving portion 16 by arranging the insert 12 with its release portion 36 facing the bone facing side 20 opposite to said insert receiving portion 16. Following that, the insert 12 is pushed along an insertion axis B and in the direction marked by arrow I into the insert receiving portion 16, until its stop portion 42 reaches the stop surface 32.

In FIG. 2, it can further be seen that the insert 12 comprises several protruding members in form of spikes 44 at its contacting region 34. These protrude transversally form the contacting region 34 and extend substantially orthogonal to the longitudinal axis L of the bone plate 14 as well as to the bone facing side 20. Furthermore, it can be seen that the spikes 44 extend beyond the bone facing side 20. In other words, they form an outermost or most outwardly protruding part at or of the bone facing side 20, due to projecting from the bone facing side 20 by a distance D (note: In FIG. 2, said distance D is marked with respect to the outer surrounding rim portion 24 of the bone facing side 20).

Accordingly, if arranged at a bone, and in particular if using more than only one insert 12, the bone plate 14 will be lifted off an adjacent bone surface and arranged at a distance thereto. Specifically, the rim portion 24 of the bone facing side 20 will be arranged with a distance D to said bone, which is instead merely contacted by the spikes 44. Overall, this may help to limit a total area of contact between the bone plate system 10 and the bone to be treated.

Further characteristics of the insert 12 and in particular of its coupling portion 40 will now be described with reference to FIG. 3, which shows a perspective view of the insert 12 as used in the above-described embodiment. Again, one can see that the coupling portion 40 comprises the diameter-enlarged stop portion 42 for contacting the stop surface 32 of the insert receiving portion 16. Furthermore, one can see that the coupling portion 40 comprises several outer plate-type members 46 which extend parallel to and along the insertion axis B of the insert 12. Further inner plate members 48 are arranged in parallel to and behind the outer plate members 46 (see also FIG. 2 and the inner plate members 48 being arranged closer to the insertion axis B than the outer plate members 46). In total, the insert 12 comprises four pairs of inner and outer plates 46, 48.

The inner plate members 48 further comprise enlarged operating portions 50 at their free ends which form the release portion 36 discussed above. Furthermore, a cover member 52 is provided and connected to the diameter-widened stop portion 42 by means of a column 54 (see also FIG. 2). Note that the insert 12 further has a longitudinal axis C which coincides with the insertion axis B in the state depicted in FIG. 2.

In general, each of the inner and outer plate members 46, 48 is deflectable relative to the longitudinal axis C and, in particular, deflectable radially outwardly and inwardly with respect thereto. In a relaxed state as depicted in FIG. 3, the inner plates 48 obstruct an inward deflection of the outer plates 46 and, preferably, even exert a radially outwardly acting biasing force on said outer plates 46 as depicted by arrow R in FIG. 3.

When being inserted into the insert receiving portion 16 along the insertion axis B, the operating portions 50 are deflected radially inwardly with respect to the longitudinal axis C when reaching the diameter-reduced cylindrical portion 27 of the insert receiving portion 16. Accordingly, they move away from the outer plates 46, thus no longer exerting a biasing force thereon and allowing for a similar inward deflection of said outer plates 46. This way, the coupling portion 40 can be pushed into the cylindrical portion 27.

Figure 3:
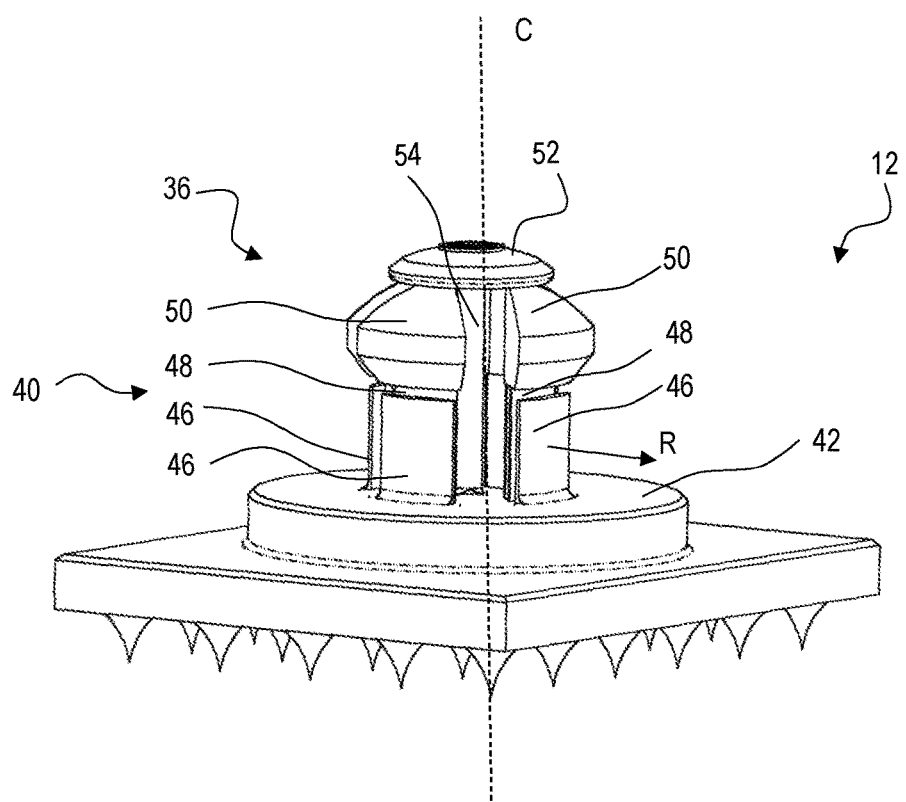
FIG. 3 shows a perspective view of the insert used in the bone plate system of the first embodiment.

When reaching the countersunk portion 28, the operating portions 50 and the inner plates 48 snap back to assume their initial position as depicted in FIG. 3. Accordingly, the outer plates 46 are forced into a close contact with a wall surface of the cylindrical portion 27 by again experiencing a biasing force from the inner plates 48. This way, the inserts 12 can be held in the insert receiving portions by means of a press or friction fit between the coupling portion 40 and the cylindrical portion 27 of the insert receiving portion 16. Note that this snap-back effect of the inner plates 48 also provides a locking function along with a form fit between the relatively large operating portions 50 and the smaller diameter of the cylindrical portion 27.

For releasing the insert 12, the operating portions 50 can be manually deflected radially inwardly (i.e., towards the insertion or longitudinal axis B, C). This way, the biasing force is again removed so that the outer plates 46 are pushed less hard against the opposite wall surfaces of the cylindrical portion 27 and can generally deflect inwardly. Following that, a pushing force which is oriented oppositely to arrow I of FIG. 2 can be exerted on the insert 12 to push it out of the insert receiving portion 16 along the insertion axis B. Consequently, the insert 12 is released by accessing the release portion 36 formed by the operating portions 50 from the front side 18 of the bone plate 14, while the actual removal of the insert 12 includes pushing it out of the bone plate 14 at or from the bone facing side 20.

Figure 4:
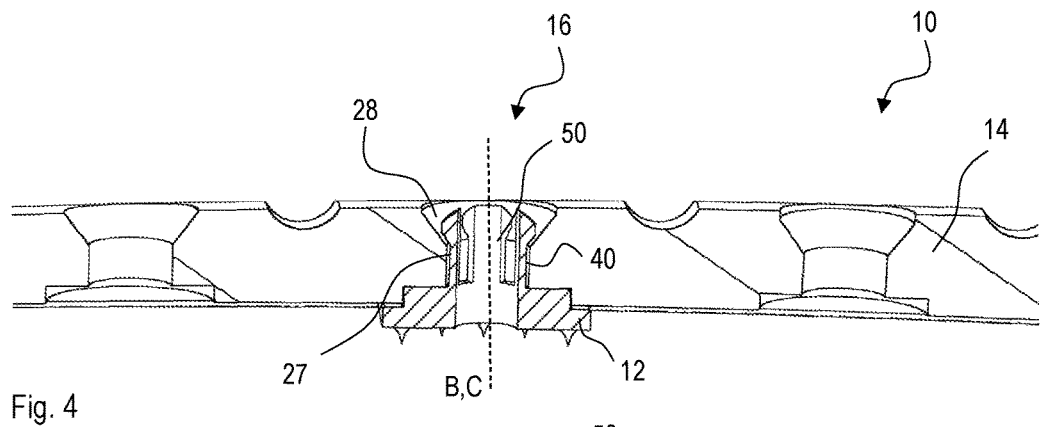
FIG. 4 shows a cross-sectional partial view of a bone plate system comprising an insert according to a second embodiment.
Figure 5:
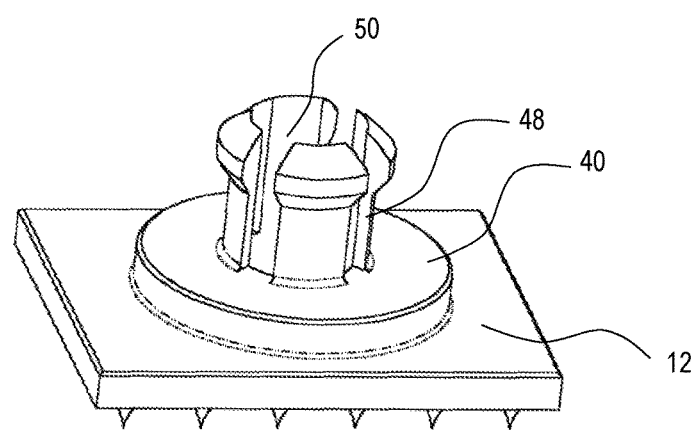
FIG. 5 shows a perspective view of the insert according to the second embodiment.

In FIGS. 4 and 5, a bone plate system 10 according to a second embodiment is shown. This embodiment differs from the first embodiment only with regard to the design of the insert 12. Specifically, the insert 12 is designed to receive a non-depicted fixing member in form of a bone screw.

For doing so, the insert 12 comprises a central through-hole 50 extending along the longitudinal axis C as well as the insertion axis B coinciding therewith. Accordingly, a bone screw can be inserted into the insert receiving portion 16 and the insert 12 to secure the bone plate 14 at a bone in an as such known manner. Note that as depicted in FIG. 5, the coupling portion 40 of the insert 12 only comprises the inner plates 48 having the enlarged operating portions 50 as discussed with reference to FIG. 3. In a relaxed state, the plate members 48 define a cross-section of the insert 12 exceeding a diameter of the cylindrical portion 27 of the insert receiving portion 16. Thus, similar to the first embodiment, the operating portions 50 and the plates 48 are at first inwardly deflected when inserting the insert 12 into said receiving portion 16 and the operating portions 50 snap back when reaching the countersunk portion 28. This way, a press/friction fit between the coupling portion 40 and insert receiving portion 16 is again formed which is releasable by operating the operating portions 50 in a similar manner as discussed with respect to the first embodiment.

Figure 6:
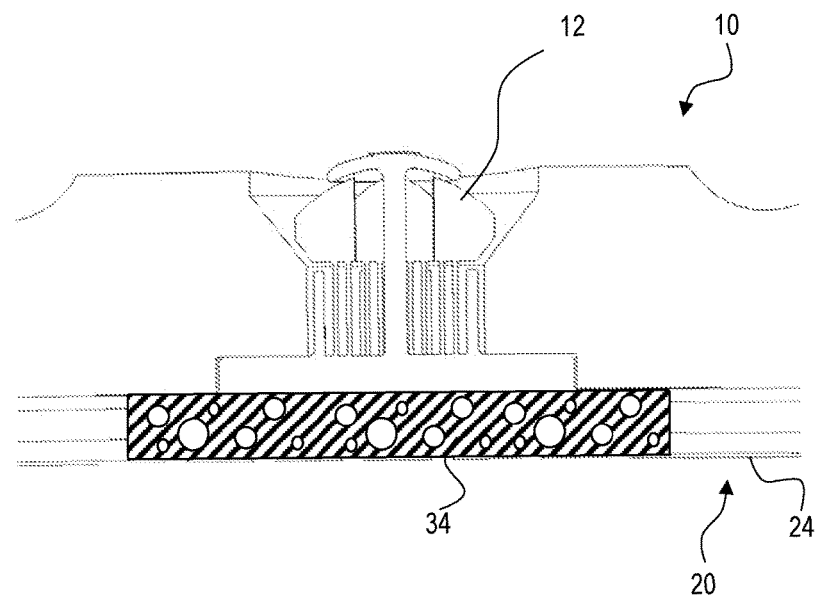
FIG. 6 shows a cross-sectional partial view of a bone plate system comprising a insert having a porous contacting region according to a third embodiment.

FIG. 6 shows a cross-sectional partial view of a bone plate system according to a third embodiment, said view being generally similar to FIGS. 2 and 4. Again, the third embodiment differs from the previous ones with respect to the insert 12. Specifically, the insert 12 comprises a contacting region 34 which is free of any protruding spikes. Instead, it comprises a bone ingrowth material, thus forming a bone ingrowth portion of the bone plate system 10.

In more detail, the contacting region 34 comprises a porous material into which the recovering bone tissue can grow. Accordingly, the insert 12 can interlock with said recovering bone tissue by means of the bone ingrowth portion of the contacting region 34. Note that in this embodiment, the insert 12 is designed such that the bone contacting region 34 does not extend beyond the bone facing side 20 and in particular beyond the rim portion 24 thereof. Rather, the bone contacting region 34 is substantially flush therewith. Also, it is generally contemplated that protruding members, such as the spikes 44 of FIG. 2, and a bone ingrowth portion may be combined in one and the same bone contacting region 34 of an insert 12.

Figure 7:
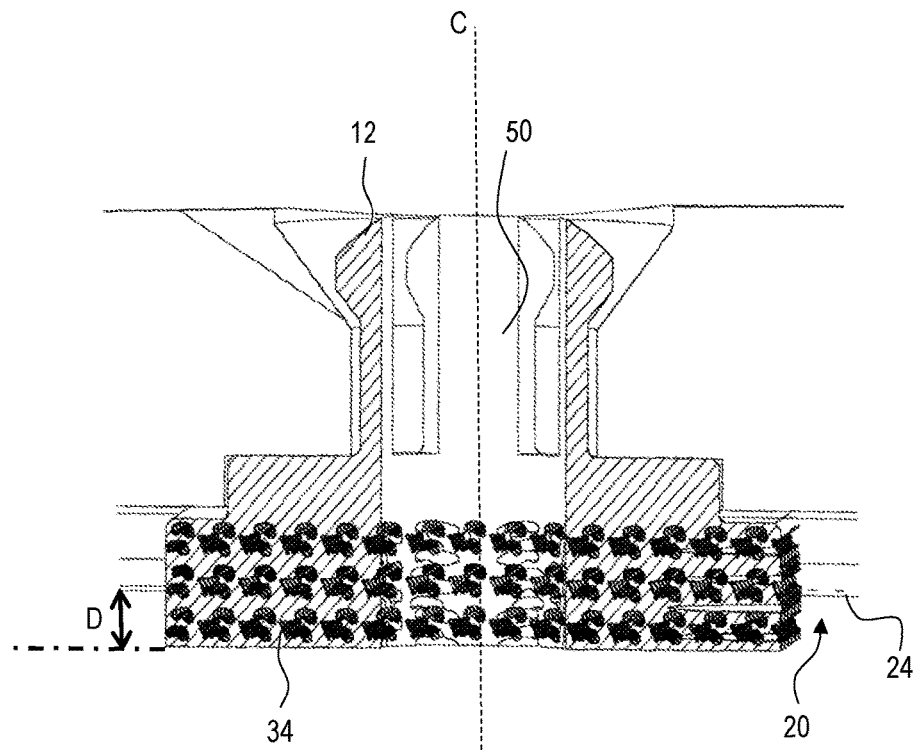
FIG. 7 shows a cross-sectional partial view of a bone plate system comprising an insert according to a fourth embodiment.
Figure 8:
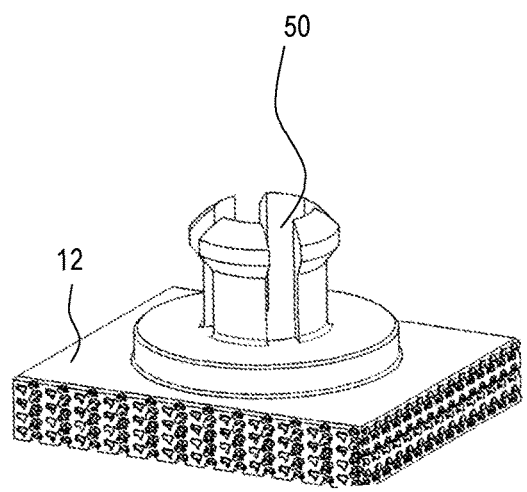
FIG. 8 shows a perspective view of the insert according to the fourth embodiment.

In FIGS. 7 and 8, views of an insert 12 according to a further embodiment are shown. Said insert 12 again has a contacting region 34 comprising a porose bone ingrowth material. Note that the porosity of said material is illustrated differently from FIG. 6 but that generally the same material can be used.

The insert 12 is further configured similarly to the embodiment according to FIGS. 4 and 5 by comprising a fixing member receiving portion in form of a central through-hole 50 along its longitudinal axis C. Also, contrary to the embodiment of FIG. 6, the insert 12 extends beyond the bone facing side 20, thus protruding therefrom as previously discussed with respect to FIG. 2. Accordingly, the insert 12 defines a distance D between an outer external surface of the insert's contacting region 34 and the rim portion 24 of the bone facing side 20.

In the forgoing, embodiments and variants of embodiments have exemplarily been described. The present invention should not be construed as being limited to the particular embodiments and their variants as discussed herein. Rather, it will be appreciated that various changes and modifications may be made by a person skilled in the art without departing from the scope of the present invention as defined in the claims that follow.

The invention claimed is:

1. A bone plate system, comprising:
   a bone plate having a bone facing side, a front side arranged substantially opposite to and facing away from the bone facing side, and an insert receiving portion; and
   an insert defining a contact region for contacting an adjacent bone surface of a bone and being releasably receivable in the insert receiving portion,
   wherein the insert is insertable into the insert receiving portion from the bone facing side, and
   wherein the contact region is configured for interlocking with the bone such that the insert remains in contact with the bone when secured to the bone and separated from the bone plate.

2. The bone plate system of claim 1, wherein the insert comprises a release portion accessible from the front side of the bone plate.

3. The bone plate system of claim 1, further comprising:
   a fixing member receiving portion configured to receive a fixing member for securing the bone plate to a bone, the fixing member receiving portion and the insert receiving portion being at least partially separated from one another.

4. The bone plate system of claim 1, wherein the insert further comprises a fixing member receiving portion configured to receive a fixing member for securing the bone plate to a bone.

5. The bone plate system of claim 1, wherein the insert receiving portion comprises a recess that is connected to the front side.

6. The bone plate system of claim 1, wherein the insert is configured to engage the insert receiving portion.

7. The bone plate system of claim 6, wherein the insert comprises a stop portion configured to abut against the insert receiving portion so as to limit an insertion depth of the insert.

8. The bone plate system of claim 1, wherein at least one of the insert and insert receiving portion comprises a locking portion for being lockable with the respective other of the insert and insert receiving portion.

9. The bone plate system of claim 8, wherein the locking portion comprises a snap-fit portion.

10. The bone plate system of claim 1, wherein the contact region is configured to extend beyond an adjacent portion of the bone facing side towards an adjacent bone surface.

11. The bone plate system of claim 1, wherein the contact region is configured to be flush with an adjacent portion of the bone facing side.

12. The bone plate system of claim 1, wherein the contact region is larger than the insert receiving portion.

13. The bone plate system of claim 1, wherein the contact region comprises a plurality of protruding members arranged to protrude towards an adjacent bone surface.

14. The bone plate system of claim 13, wherein the protruding members comprise spikes.

15. The bone plate system of claim 1, wherein the contact region comprises a bone ingrowth portion.

16. The bone plate system of claim 1, wherein the contact region comprises a porous material.

17. A bone plate system, comprising: a bone plate having a bone facing side, a front side arranged substantially opposite to and facing away from the bone facing side, and an insert receiving portion; and an insert defining a contact region and a release portion, the contact region for contacting an adjacent bone surface and the release portion being releasably receivable in the insert receiving portion, wherein the insert is insertable into the insert receiving portion from the bone facing side, and wherein the insert includes at least one deflectable operating portion that in a first position inhibits removal of the insert from the insert receiving portion of the bone plate and in a second position allows removal of the insert from the insert receiving portion; and wherein the contact region is configured for interlocking with the bone such that the insert remains in contact with the bone when secured to the bone and separated from the bone plate.

18. The bone plate system of claim 17, wherein the release portion is accessible from the front side of the bone plate.

19. The bone plate system of claim 1, further comprising:
   a fixing member receiving portion configured to receive a fixing member for securing the bone plate to a bone, the fixing member receiving portion and the insert receiving portion being at least partially separated from one another.

20. A method of operating a bone plate system comprising a bone plate and an insert, the bone plate having a bone facing side, a front side being arranged substantially opposite to and facing away from the bone facing side, and an insert receiving portion, the insert defining a contact region for contacting an adjacent bone surface of a bone and being releasably receivable in the insert receiving portion, the method comprising the steps of:
- arranging the bone plate such that the contact region of the insert releasably receivable in the insert receiving portion abuts against the adjacent bone surface of the bone;
- securing the bone plate to the bone by way of at least one fixing member; and
- removing the at least one fixing member and releasing the insert from the insert receiving portion of the bone plate such that the bone plate can be removed from the bone while the insert remains in contact with the adjacent bone surface of the bone.

21. A bone plate system, comprising: a bone plate having a bone facing side, a front side being arranged substantially opposite to and facing away from the bone facing side, and an insert receiving portion; and an insert defining a contact region for contacting an adjacent bone surface and being releasably receivable in the insert receiving portion, wherein the insert is insertable into the insert receiving portion from the bone facing side, and wherein the contact region is configured to be substantially parallel to the bone facing side and to exceed a largest cross-section of the insert receiving portion; and wherein the contact region is configured for interlocking with the bone such that the insert remains in contact with the bone when secured to the bone and separated from the bone plate.

* * * * *

UNITED STATES PATENT AND TRADEMARK OFFICE
CERTIFICATE OF CORRECTION

PATENT NO. : 10,383,667 B2  
APPLICATION NO. : 15/229966  
DATED : August 20, 2019  
INVENTOR(S) : Torres et al.

Page 1 of 1

It is certified that error appears in the above-identified patent and that said Letters Patent is hereby corrected as shown below:

On the Title Page

Item (72), Line 3, Kennan Hanson, Sloatsburg, NY, delete "Kennan" and insert --Keenan--.

Item (72), Line 5, Zongtau Zhang, Riverdale, NJ, delete "Zongtau" and insert --Zongtao--.

Signed and Sealed this  
Eighteenth Day of February, 2020

Andrei Iancu  
*Director of the United States Patent and Trademark Office*